US00PP26949P3

(12) United States Plant Patent
De Groot

(10) Patent No.: US PP26,949 P3
(45) Date of Patent: Jul. 19, 2016

(54) MINIATURE ROSE PLANT NAMED 'RUIPE0306C'

(50) Latin Name: ***Rosa* L.**
Varietal Denomination: RUIPE0306C

(71) Applicant: De Ruiter Intellectual Property B.V., Amstelveen (NL)

(72) Inventor: Hendrikus C. A. De Groot, Amstelveen (NL)

(73) Assignee: De Ruiter Intellectual Property B.V., Amstelveen (NL)

( * ) Notice: Subject to any disclaimer, the term of this patent is extended or adjusted under 35 U.S.C. 154(b) by 93 days.

(21) Appl. No.: 14/120,945

(22) Filed: Jul. 14, 2014

(65) Prior Publication Data

US 2015/0313049 P1 Oct. 29, 2015

(30) Foreign Application Priority Data

Apr. 28, 2014 (QZ) ..... PBR 2014/1150

(51) Int. Cl.
*A01H 5/02* (2006.01)

(52) U.S. Cl.
USPC ..... Plt./119

(58) Field of Classification Search
USPC ..... Plt./105, 126, 146, 119
See application file for complete search history.

(56) References Cited

PUBLICATIONS

New Plants and Flowers. Dutch rose breeder extends indoor/outdoor patio series Jul. 29, 2013, retrieved on Dec. 9, 2015, retrieved from the Internet at <http://www.newplantsandflowers.com/dutch-rose-breeder-extends-indooroutdoor-patio-series> 3 pp.*

* cited by examiner

*Primary Examiner* — June Hwu
(74) *Attorney, Agent, or Firm* — Barbara Campbell; Cochran Freund & Young LLC

(57) ABSTRACT

A new Rose plant particularly distinguished by having orange flowers and a mostly upright form, is disclosed.

2 Drawing Sheets

Genus and species: *Rosa* L.
Variety denomination: 'RUIPE0306C'.

CROSS REFERENCE TO RELATED APPLICATIONS

This application claims, under 35 U.S.C. §119, priority to and the benefit of European Community Plant Variety Rights Application No. 2014/1150, filed Apr. 28, 2014, the entire contents of which are incorporated herein by reference for all purposes.

BACKGROUND OF THE NEW PLANT

The present invention comprises a new and distinct variety of Rose, botanically known as *Rosa* L., and hereinafter referred to by the variety name 'RUIPE0306C'. 'RUIPE0306C' originated from a cross conducted in May 2004 in Hazerswoude, The Netherlands between the proprietary female *Rosa* variety 'P-01-0152-001' (unpatented), and the proprietary male *Rosa* variety 'Ruira013a' (unpatented).

The seeds from the cross were sown and plants were grown for evaluation in a greenhouse without heating. An individual plant designated 'RUIPE0306C' was selected in January 2006. 'RUIPE0306C' was first vegetatively propagated in May 2006 in Hazerswoude, The Netherlands by branch cuttings. 'RUIPE0306C' was found to reproduce true to type in successive generations of asexual propagation via branch cuttings.

SUMMARY

The following are the most outstanding and distinguishing characteristics of this new variety when grown under normal horticultural practices in Hazerswoude, The Netherlands.

1. Orange flowers; and
2. A mostly upright form.

DESCRIPTION OF THE PHOTOGRAPHS

This new Rose plant is illustrated by the accompanying photographs which show the plant's overall plant habit including form, foliage, buds, and flowers. The colors shown are as true as can be reasonably obtained by conventional photographic procedures. FIG. 1 is of 24-week-old plant grown indoors in Amstelveen, The Nertherlands and taken in January 2014 and FIG. 2 is of the plants parts taken from the 24-week-old plant.

Figure 1:
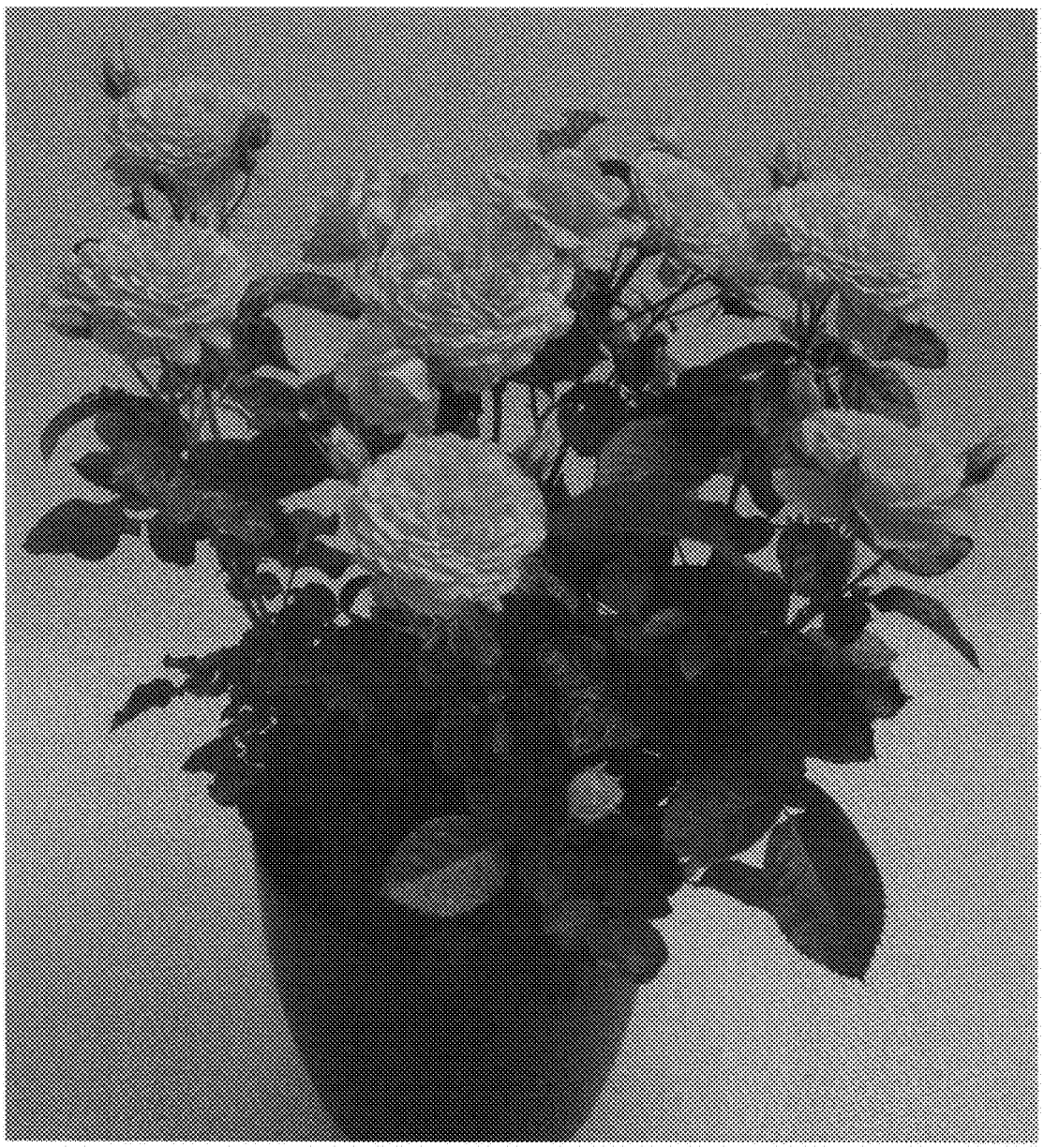
FIG. 1 shows the overall plant habit, including the blooms, buds, and foliage, in a pot.
Figure 2:
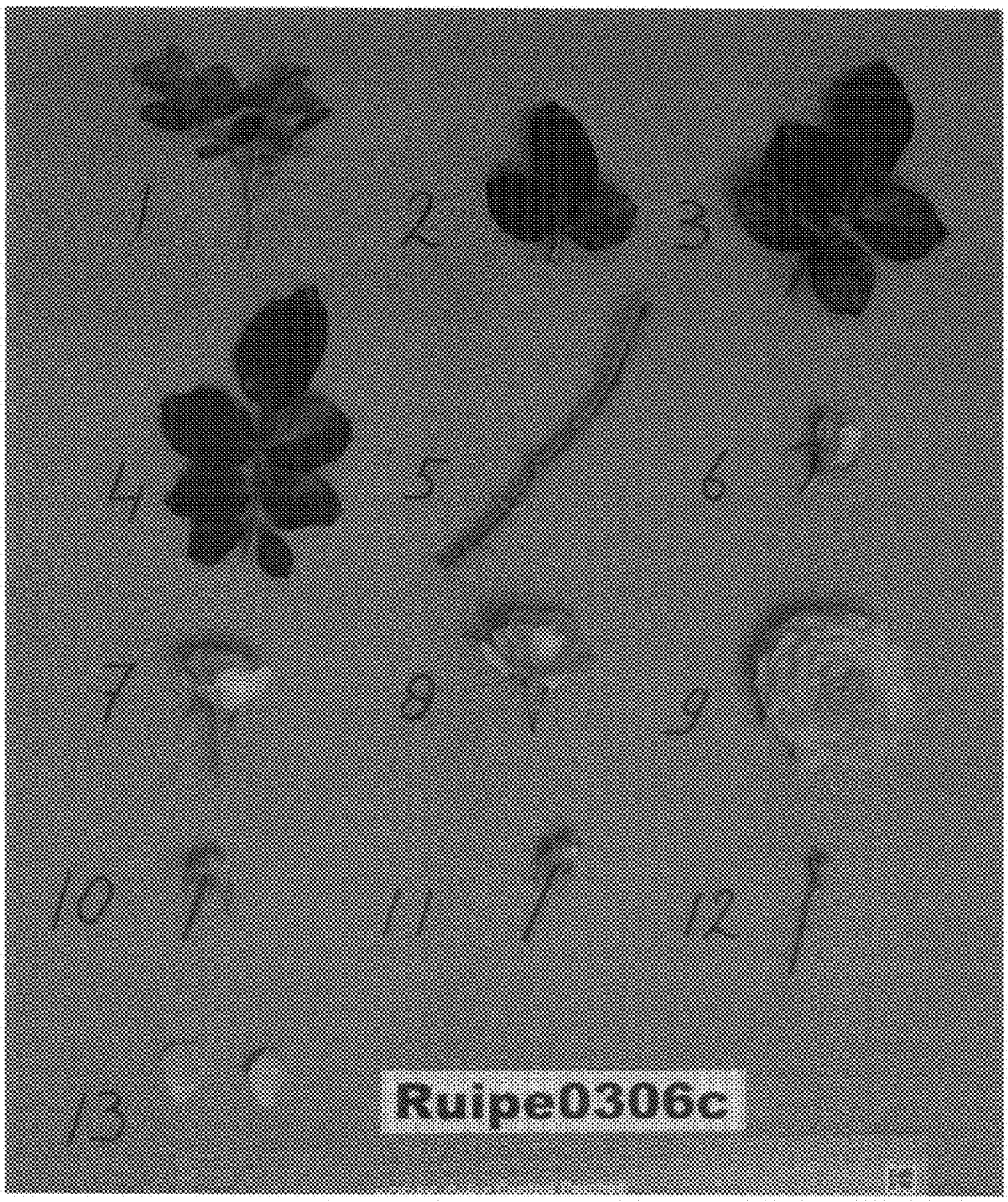
FIG. 2 shows a close-up of individual flower parts of the plant, where.

1 shows immature leaves and leaflets.
2 shows a leaf having 3 leaflets.
3 shows a leaf having 5 leaflets.
4 shows a leaf having 7 leaflets.
5 shows a portion of a stem with thorns
6 show a side view of a flower in immature bloom
7 shows a side view of a flower in immature bloom.
8 shows a side view of a flower in immature bloom.
9 shows a mature flower in bloom.

10 shows a side view of the sepals and reproductive organs after bloom.

11 shows a side view of the sepals and reproductive organs after bloom.

12 shows a side view of the reproductive organs without the sepals.

13 shows the upper and lower surfaces of individual petals.

DESCRIPTION OF THE NEW VARIETY

The following detailed descriptions set forth the distinctive characteristics of 'RUIPE0306C'. The data which define these characteristics were collected from 24-week-old plants grown in a glasshouse in Amstelveen, The Netherlands in January 2014. Color references are to The R.H.S. Colour Chart of The Royal Horticultural Society of London (R.H.S.), 1995.

Classification:

*Family*.—Rosaceae.

*Botanical*.—*Rosa* L.

*Designation*.—'RUIPE0306C'.

*Parentage*.—Female parent: The proprietary female rose variety 'P-01-0152-001' (unpatented). Male parent: The proprietary male rose variety 'Ruira013a' (unpatented).

Plant:

*Height*.—30.0 cm to 40.0 cm.

*Spread*.—30.0 cm.

*Form*.—Mostly upright.

*Time to produce a rooted cutting*.—Average is 4 weeks.

*Time to bloom from propagation*.—Average is 10 weeks.

*Lastingness of inflorescence on the plant*.—Average is 3 weeks.

*Commercial classification*.—Miniature.

Lateral branches/peduncles:

*Color*.—RHS 138A.

*Pubescence*.—Absent.

*Stem shape and appearance*.—Rounded and glossy.

*Diameter*.—Average is 0.4 cm.

*Length*.—Average is 20.0 cm.

*Internode length*.—Average is 3.0 cm.

*Anthocyanin*.—Absent.

*Anthocyanin in young shoot*.—Absent.

*Thorns*.—Density (quantity per unit area): Average is 13 to 15 thorns per stem. Shape: Concave. Color: RHS 163C. Length: 1.2 cm. Width (at the base): Average is 0.7 cm.

Foliage:

*Arrangement and type*.—Compound, imparipinnate.

*Quantity of leaflets per leaf*.—3, 5, or 7 leaflets per leaf.

*Leaf length*.—Average is 12.0 cm.

*Leaf width*.—Average is 11.0 cm.

*Anthocyanin*.—Absent.

*Terminal leaflet*.—Length: 5.5 cm. Width: 3.5 cm. Shape: Ovate. Apex: Acute. Base: Round. Margin: Serrate. Color, immature leaf: Upper surface: RHS 137B. Lower surface: RHS 200C. Color, mature leaf: Upper surface: RHS 139A. Lower surface: RHS 147B. Texture: Upper surface: Glabrous, leathery. Lower surface: Glabrous.

*Lateral leaflet*.—Length: Average is 5.0 cm. Width: Average is 3.4 cm. Shape: Ovate. Apex: Acute. Base: Round. Margin: Serrate. Color, immature leaf: Upper surface: RHS 137B. Lower surface: RHS 200C. Color, mature leaf: Upper surface: RHS 139A. Lower surface: RHS 147B. Texture: Upper surface: Glabrous, leathery. Lower surface: Glabrous.

*Leaflet venation pattern*.—Pinnate.

*Leaflet venation color*.—Upper surface: RHS 176B. Lower surface: RHS 147C.

*Petiole of the leaf*.—Length: 1.2 cm. Diameter: 0.1 cm. Color: RHS 147A. Texture: Pubescent. Thorns: Present; deep concave in shape and 0.6 cm in length.

*Petiole of the leaflet*.—Length: 0.1 cm. Diameter: 0.1 cm. Color: RHS 138B. Texture: Pubescent. Thorns: Absent.

*Stipules*.—Length: average: 0.8 cm. Width: average: 0.4 cm. Appearance: Scale-like. Apex: Auricles about 0.5 cm in length and 0.1 cm in width. Base: Normal. Margin: Entire. Color, immature leaf: Upper surface: RHS 138B. Lower surface: RHS 137C. Color, mature leaf: Upper surface: RHS 138B. Lower surface: RHS 137C. Texture (both upper and lower surfaces): Smooth.

Flowers or inflorescence:

*Appearance and arrangement*.—Flowers are born single on peduncle, sometimes in a large spray, there are 3 to 4 flowers.

*Fragrance*.—Very light.

*Diameter*.—Average is 7.0 cm.

*Depth or height*.—Average is 4.0 cm.

*Lastingness of flowers on the plant*.—Average is 14 to 16 days.

*Flower type*.—Double.

*Buds*.—Length: Average is 2.5 cm. Width: Average is 1.5 cm. Shape: Ovate. Color: RHS 31B.

*Petals*.—Quantity per flower: Average is 50 petals. Length: Average is 2.8 cm. Width: Average is 2.5 cm. Shape: Shell-shaped. Apex: Mucronulate. Base: Cuneate. Margin: Reflexing. Color, when opening: Upper surface: RHS 30D. Lower surface: RHS 28D. Color, when fully open: Upper surface: RHS 30D with a basal spot of RHS 14C (Yellow); size is medium. Lower surface: RHS 28D. Surface texture (both upper and lower surfaces): Velvety. Petaloids: Absent.

*Sepals*.—Quantity per flower: 5. Length: 27.0 mm. Width: 9.0 mm. Shape: Ensiform. Apex: Acute with sometimes a slight curvature. Base: Truncate. Margin: Ciliate. Sepal extension: Absent or very weak. Color: Upper surface: Between RHS 139B and RHS 139C. Lower surface: RHS 138A.

*Surface texture*.—Upper surface: Pubescent. Lower surface: Pubescent.

Reproductive organs:

*Stamens*.—Quantity per flower: Average is 85. Anther color: RHS 22C. Anther shape: Bi-lobate. Filament length: 0.5 cm.

*Pistils*.—Quantity per flower: Average is 13. Pistil length: Average is 0.4 cm. Stigma shape: Fan-shaped. Stigma color: RHS 163C. Style length: Average is 0.6 cm. Style color: RHS 43A. Receptacle: Height: 1.3 cm. Diameter: 1.5 cm. Color: RHS 144B. Shape: Round globe. Texture: smooth.

Fruit and seed set: None observed to date.

Disease and pest/insect resistance: Mildrew resistant, insect resistance not observed.

COMPARISON WITH PARENTAL LINES AND KNOWN VARIETY

'RUIPE0306C' is a distinct variety of Rose and is distinguished from its parents as described in Table 1.

TABLE 1

| Comparison with Parental Lines | | | |
|---|---|---|---|
| Characteristic | 'RUIPE0306C' | Female Parent 'P-01-0152-001' | Male Parent 'Ruira013a' |
| Flower color | Orange | Orange-red | Orange pink |

When 'RUIPE0306C' is compared to the commercial variety 'RUIPE0306D', the following differences are described in Table 2.

TABLE 2

| Comparison with Similar Variety | | |
|---|---|---|
| Characteristic | 'RUIPE0306C' | 'RUIPE0306D' |
| Flower color | Orange | Orange-pink |
| Average number of petals per flower | 50 | 30 to 35 |

I claim:

1. A new and distinct variety of Rose plant designated 'RUIPE0306C' as illustrated and described herein.

* * * * *